United States Patent
Wahl et al.

(10) Patent No.: US 9,358,032 B2
(45) Date of Patent: Jun. 7, 2016

(54) SURGICAL DEVICE USING WATER JET AND METHOD FOR OPERATING SAID DEVICE

(75) Inventors: Hans-Juergen Wahl, Trochtelfingen (DE); Alexander Pfaeffle, Gomaringen (DE); Ralf Kuehner, Stuttgart (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 810 days.

(21) Appl. No.: 12/741,516

(22) PCT Filed: Nov. 4, 2008

(86) PCT No.: PCT/EP2008/009290
§ 371 (c)(1),
(2), (4) Date: Jul. 8, 2010

(87) PCT Pub. No.: WO2009/059742
PCT Pub. Date: May 14, 2009

(65) Prior Publication Data
US 2011/0004232 A1    Jan. 6, 2011

(30) Foreign Application Priority Data

Nov. 6, 2007    (DE) .................. 10 2007 052 805

(51) Int. Cl.
*A61B 17/3203*    (2006.01)
*A61B 19/00*    (2006.01)
*A61B 17/00*    (2006.01)

(52) U.S. Cl.
CPC ... *A61B 17/3203* (2013.01); *A61B 2017/00199* (2013.01); *A61B 2019/448* (2013.01); *A61B 2019/463* (2013.01); *A61B 2019/464* (2013.01)

(58) Field of Classification Search
CPC ...................... A61B 17/3203; A61B 17/32037; A61B 2017/32032; B24C 5/02; B26F 1/26
USPC ........ 606/159, 167, 169, 170; 604/19, 68, 69, 604/70, 22–26, 65–67; 83/53, 177; 600/139–151, 585; 433/80; 451/40, 75, 451/102; 29/81.08; 601/154, 162; 73/861, 73/861.39; 417/211.5, 274
See application file for complete search history.

(56) References Cited

U.S. PATENT DOCUMENTS

| 4,655,742 A | 4/1987 | Vantard |
| 4,850,377 A | 7/1989 | Parker et al. |
| 5,255,669 A | 10/1993 | Kubota et al. |

(Continued)

FOREIGN PATENT DOCUMENTS

| DE | 92 00 452 U1 | 7/1992 |
| EP | 0 879 578 A1 | 11/1998 |

(Continued)

*Primary Examiner* — Ryan J Severson
*Assistant Examiner* — Rachel S Papeika
(74) *Attorney, Agent, or Firm* — Blank Rome LLP

(57) ABSTRACT

A water jet surgical device comprises a fluid feed device, which is controllable by control signals from a control device, for delivering a fluid into a connecting line of a surgical instrument with an outlet nozzle. The fluid feed device includes at least one measuring device, which is configured such that following the connection of the surgical instrument to the fluid feed device, the measuring device generates measuring signals to represent a quantity of fluid delivered. The quantity of fluid delivered may be displayed on a display or recorded in a recording unit. This enables improved monitoring of surgical operations.

7 Claims, 1 Drawing Sheet

(56) References Cited

U.S. PATENT DOCUMENTS

| | | | |
|---|---|---|---|
| 5,322,504 A | 6/1994 | Doherty et al. | |
| 5,505,729 A | 4/1996 | Rau | |
| 5,536,242 A * | 7/1996 | Willard et al. | 604/30 |
| 5,584,671 A * | 12/1996 | Schweitzer, Jr. | A61M 5/142 137/545.4 |
| 6,396,583 B1 * | 5/2002 | Clare | 356/436 |
| 7,083,719 B2 * | 8/2006 | Bowman, Jr. | A61M 1/28 210/143 |
| 7,553,318 B2 * | 6/2009 | Ammann | 606/167 |
| 2003/0160063 A1 * | 8/2003 | Paukovits et al. | 222/129 |
| 2004/0138687 A1 * | 7/2004 | Himes | 606/167 |
| 2005/0059924 A1 | 3/2005 | Katz et al. | |
| 2005/0228423 A1 * | 10/2005 | Khashayar et al. | 606/167 |
| 2006/0156875 A1 * | 7/2006 | McRury et al. | 83/13 |
| 2006/0247743 A1 | 11/2006 | Hayakawa et al. | |
| 2008/0221602 A1 * | 9/2008 | Kuehner et al. | 606/167 |

FOREIGN PATENT DOCUMENTS

| | | |
|---|---|---|
| JP | 1-314557 A | 12/1989 |
| JP | 2001-161706 A | 6/2001 |
| JP | 2003-24442 A | 1/2003 |
| JP | 2006-122307 A | 5/2006 |
| JP | 2006-198409 A | 8/2006 |
| JP | 2007-507261 A | 3/2007 |

* cited by examiner

SURGICAL DEVICE USING WATER JET AND METHOD FOR OPERATING SAID DEVICE

FIELD OF THE INVENTION

Embodiments of the invention relate to a water jet surgical device having a fluid feed device including a measuring device and a method for operating said surgical device.

BACKGROUND

Water jet surgical devices by means of which tissue can be parted using a high pressure water jet are generally known. When a device of this type is used for open surgery, drainage of the "cutting fluid" is not problematic. However, when devices of this type are used for endoscopic operations, that is, within body cavities, problems can arise due to the influx of cutting fluid.

SUMMARY

It is an object to provide a water jet surgical device of the aforementioned type such that the problems arising, particularly during endoscopic operations, are lessened.

This object is achieved with a water jet surgical device comprising a fluid feed device, which is controllable by control signals from a control device, for delivering a fluid into a connecting line of a surgical instrument with an outlet nozzle. The at least one measuring device is provided and is configured such that following the connection of the surgical instrument to the fluid feed device, the measuring device generates measuring signals to represent a quantity of fluid delivered. The quantity of fluid delivered can then be displayed on a display or recorded in a recording unit. It is therefore possible, during an operation, to determine the quantity of cutting fluid introduced into a body cavity and to compare said quantity with the fluid quantity drawn out of the operation area. It is also possible to undertake precise planning of the operation, specifically with regard to the quantity of the cutting fluid used, which must be made available in a reservoir.

The measuring device preferably comprises a fill level sensor and generates a full signal when the connecting line of the surgical instrument is substantially filled as far as the outlet nozzle and issues a filling quantity signal needed for filling the connecting line. By this mechanism, the water jet surgical device can be made ready for functioning such that when the surgeon issues a start signal to begin a cutting procedure, cutting fluid is actually present at the outlet nozzle.

The display or registration unit is preferably configured so that the quantity of fluid delivered minus the filling quantity is displayed. This filling quantity can be relatively large, particularly in the case of long connecting lines or surgical instruments with a large fluid capacity. As such, to prevent false reporting of the measurement of the fluid quantity dispensed into the body, the filling quantity must not be included.

An input device is preferably provided, by which a quantity signal corresponding to the surgical instrument attached can be passed to the control device to deliver a fluid quantity to be delivered by the fluid feed device. In this embodiment of the invention, a quantity of cutting fluid that is delivered by the fluid feed device is predetermined, so that it is possible to be sure that the device is filled without necessarily measuring when the connecting line or the surgical instrument is filled.

This input of the fluid quantity can be predetermined with a manually operated input device. In a preferred embodiment of the invention, the fluid quantity necessary for filling the surgical instrument and the connecting line thereof is communicated directly to the input device by an encoding device in the surgical instrument, so that manual programming is not needed.

If a fill level sensor is present, said sensor may be configured as a pressure sensor that generates the full signal after sensing a predetermined pressure change or a predetermined pressure variation over time. In general, the pressure of the cutting fluid is low for as long as air is being forced out of the outlet nozzle.

In another embodiment of the invention, the sensor device comprises a moisture sensor or conductivity sensor, which is preferably mounted very close to the outlet nozzle and generates a signal when the fluid has actually arrived at the location of the sensor.

The method for operating a water jet surgical device comprises the following steps: connecting a surgical instrument to the water jet surgical device; generating control signals for controlling a fluid feed device such that the fluid is fed to the surgical instrument until said instrument is essentially filled as far as the outlet nozzle thereof; and ending the control signals and generating an operating release signal such that operation of the fluid feed device for use of the water jet surgical device is permitted.

Actuation of the water jet surgery device is therefore prevented until the surgical instrument is really "clear to start".

BRIEF DESCRIPTION OF THE DRAWINGS

Example embodiments of the invention will now be described in greater detail making reference to the drawings, in which.

DETAILED DESCRIPTION

Figure 1:
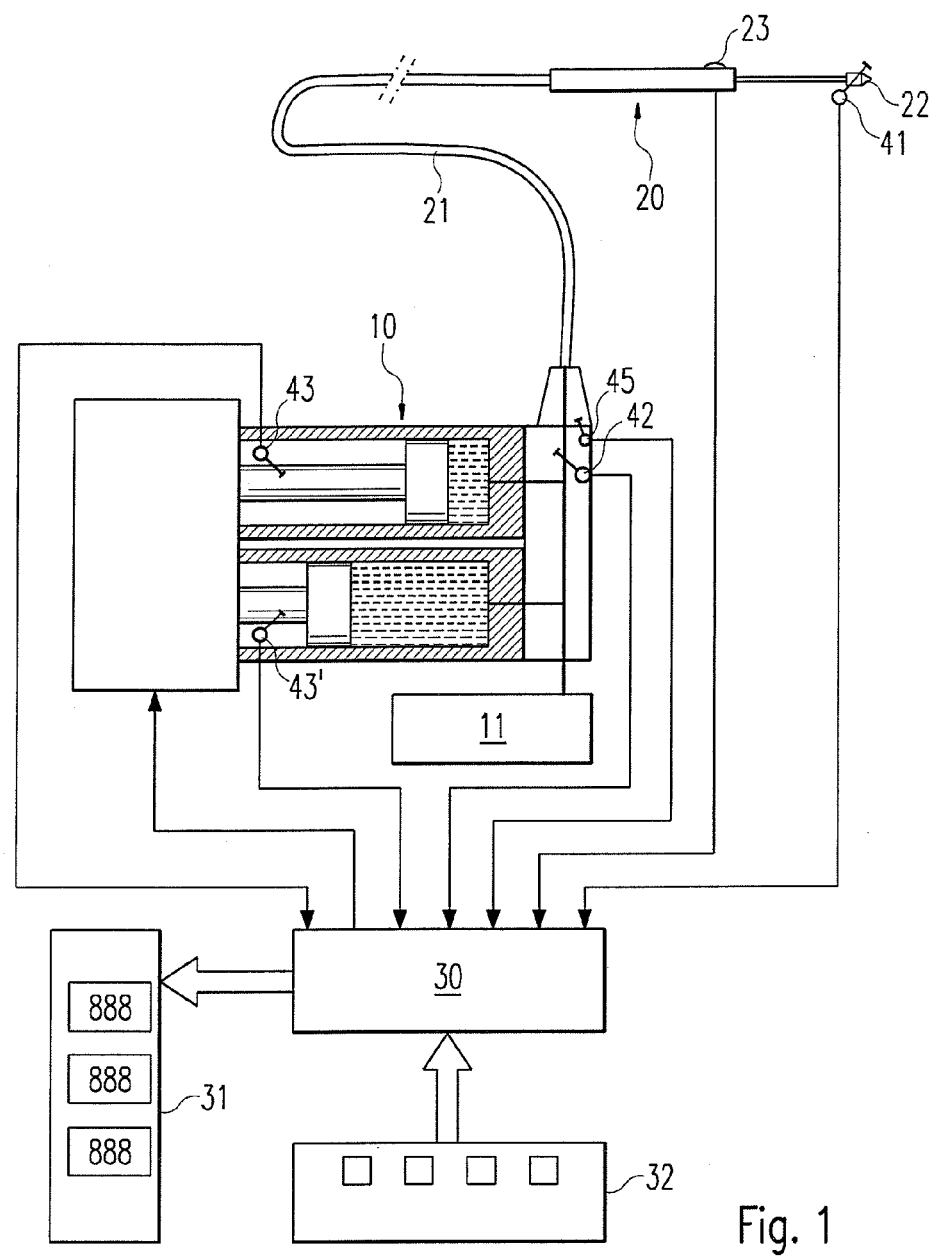
FIG. 1 is a schematic representation of an example embodiment that illustrates the different components.

FIG. 1 shows a pump with two pistons as a fluid feed device 10, which feeds the cutting fluid from a reservoir 11 via a connecting line 21 of a surgical instrument 20 to an outlet nozzle 22, from which, upon actuation of an actuating button 23, cutting fluid is ejected from the outlet nozzle 22 for parting tissue or for injection into tissue. Naturally, other pressure generating devices can be used.

In the fluid feed device 10 according to this exemplary embodiment, the position of the pistons are monitored by position sensors 43, 43'. The output signals of the sensors 43, 43' are fed to a control device 30.

A coupling feeler 45, which responds when a surgical instrument 20 is connected to the fluid feed device 10, is also provided at the fluid feed device 10.

The pressure generated by the fluid feed device 10 is sensed by a pressure sensor 42; the output signals of the pressure sensor 42 are fed to the control device 30. Alternatively or additionally, a moisture sensor 41 can be provided in the outlet nozzle 22, or at least close thereto, which responds if cutting fluid reaches the sensor 41.

The control device 30 is connected to a display unit 31 on which the various parameters, and particularly the quantity of fluid fed by the fluid feed device 10 and ejected by the outlet nozzle 22, are displayed.

Also provided is an input device 32 by which operating data can be input to the control device 30. The operating data indicates, for example, the quantity of fluid that is to be fed into the surgical instrument 20 if said instrument is to be filled as far as the outlet nozzle 22.

Therefore, if a surgical instrument 20 is connected to the fluid feed device 10, the coupling feeler 45 generates a corresponding signal that is passed to the control device 30. When a suitable "fill command" is issued, input by the surgeon via the input device 32, the fluid feed device 10 operates until the surgical instrument 20 is filled with cutting fluid as far as the outlet nozzle 22. The surgeon can then activate the device by pressing the actuating button 23, allowing a stream of cutting fluid to emerge from the outlet nozzle 22 such that a target tissue which is being aimed at is parted. The quantity of fluid output during the operation and actually emerging from the outlet nozzle 22, that is the total fed quantity, less the fluid quantity contained in the surgical instrument 20, is indicated on the display unit 31.

Figure 2:
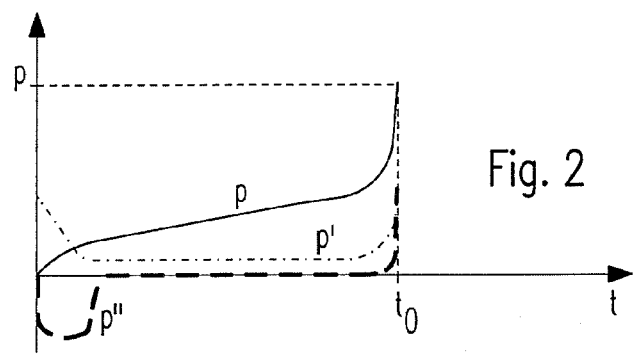
FIG. 2 is a graph that illustrates the change in pressure during filling of the surgical instrument included in FIG. 1.

FIG. 2 shows a pressure change graph in an ideal case. According to this graph, the pressure p increases while the cutting fluid is flowing in the connecting line in the direction of the outlet nozzle 22, since the air cushion which is driven ahead of the fluid becomes ever smaller. At the moment (time t0) when the cutting fluid reaches the outlet nozzle 22, the pressure rises abruptly, since the cutting fluid, by reason of the very high viscosity thereof compared with air, has a greater flow resistance at the (very small) outlet nozzle 22. This abrupt pressure increase can be used to provide a signal that indicates that the surgical instrument 20 is now correctly filled and is therefore ready for use.

It should be appreciated that the second derivative of the pressure change over time is more suitable for generating a signal of this type, since this value can only have a positive value when the aforementioned abrupt pressure rise actually occurs.

The invention claimed is:

1. A water jet surgical device, comprising:
    a fluid feed device, which is controllable by control signals from a control device, for delivering a fluid into a connecting line of a surgical instrument with an outlet nozzle; and
    a display or recording unit,
    wherein at least one measuring device is provided and is configured such that following a connection of the surgical instrument to the fluid feed device, the measuring device generates measuring signals to represent a quantity of fluid delivered, said measuring signals for use in the display or recording unit, and
    wherein the display or recording unit is configured so that the quantity of fluid delivered minus a filling quantity needed for filling the connecting line is displayed.

2. The water jet surgical device according to claim 1, wherein:
    the measuring device comprises a fill level sensor and generates a full signal when the connecting line is substantially filled as far as the outlet nozzle and issues a fill quantity signal representing the filling quantity needed for filling the connecting line.

3. The water jet surgical device according to claim 2, wherein:
    the fill level sensor comprises a pressure sensor which generates the full signal upon sensing a predetermined pressure change or a predetermined change of the pressure over time.

4. The water jet surgical device according to claim 2, wherein:
    the fill level sensor comprises a moisture sensor or a conductivity sensor.

5. The water jet surgical device according to claim 1, further comprising:
    an input device by which a quantity signal depending on the surgical instrument attached can be passed to the control device to input a fluid quantity to be delivered by of the fluid feed device.

6. The water jet surgical device according to claim 5, wherein: the input device can be manually operated.

7. The water jet surgical device according to claim 5, wherein: the input device is programmable via the surgical instrument.

* * * * *